(12) United States Patent
Nagae et al.

(10) Patent No.: US 11,733,382 B2
(45) Date of Patent: Aug. 22, 2023

(54) ULTRASONIC DIAGNOSTIC APPARATUS, LEARNING APPARATUS, AND IMAGE PROCESSING METHOD

(71) Applicant: CANON KABUSHIKI KAISHA, Tokyo (JP)

(72) Inventors: Kenichi Nagae, Kanagawa (JP); Shoya Sasaki, Kanagawa (JP); Naoya Iizuka, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 182 days.

(21) Appl. No.: 17/154,634

(22) Filed: Jan. 21, 2021

(65) Prior Publication Data
US 2021/0228184 A1 Jul. 29, 2021

(30) Foreign Application Priority Data
Jan. 24, 2020 (JP) .................................. 2020-009941

(51) Int. Cl.
*A61B 8/00* (2006.01)
*G01S 15/89* (2006.01)
(Continued)

(52) U.S. Cl.
CPC ........ *G01S 15/8977* (2013.01); *A61B 8/4444* (2013.01); *A61B 8/461* (2013.01);
(Continued)

(58) Field of Classification Search
CPC ... G01S 15/8977; A61B 8/4444; A61B 8/461; A61B 8/463; A61B 8/5207; A61B 8/54; G06N 3/08
See application file for complete search history.

(56) References Cited

U.S. PATENT DOCUMENTS

2020/0294230 A1* 9/2020 Honjo ................. A61B 8/5269
2020/0405269 A1* 12/2020 Swisher ............... A61B 8/4444

FOREIGN PATENT DOCUMENTS

JP 2009219876 A 10/2009
JP 2019025044 A 2/2019

OTHER PUBLICATIONS

Maxime Gasse, et al.; "High-Quality Plane Wave Compounding using Convolutional Neural Networks;" Labex Primes (ANR-11-LABX-0063) of Université de Lyon, within the program "Investissements d'Avenir" (ANR-11-IDEX-0007) operated by the French National Research Agency (ANR); pp. 1-3.
(Continued)

*Primary Examiner* — Christopher Koharski
*Assistant Examiner* — Taylor Deutsch
(74) *Attorney, Agent, or Firm* — Canon U.S.A., Inc. IP Division

(57) ABSTRACT

An ultrasonic diagnostic apparatus includes an ultrasonic probe configured to transmit and receives ultrasonic waves to and from an observation region of an object. The ultrasonic diagnostic apparatus further includes an estimated image generating unit configured to generate estimated image data corresponding to image data based on an ultrasonic focused beam from image data obtained by transmission of an ultrasonic plane-wave beam by using a model having been machine-learned from learning data including image data obtained by the transmission of the ultrasonic plane-wave beam and image data obtained by the transmission of the ultrasonic focused beam.

16 Claims, 11 Drawing Sheets

(51) Int. Cl.
*G06N 3/08* (2023.01)
*A61B 8/08* (2006.01)
(52) U.S. Cl.
CPC ............ *A61B 8/463* (2013.01); *A61B 8/5207* (2013.01); *A61B 8/54* (2013.01); *G06N 3/08* (2013.01)

(56) References Cited

OTHER PUBLICATIONS

Gasse, M., et al., "High-Quality Plane Wave Compounding Using Convolutional Neural Networks,", IEEE Transactions on Ultrasonics, Ferroelectrics, and Frequency Control, Oct. 2017, pp. 1637-1639, vol. 64, No. 10.

* cited by examiner

FIG. 4
| LEARNING DATA ID | INPUT DATA | | | | GROUND TRUTH DATA |
|---|---|---|---|---|---|
| | PLANE-WAVE BEAM IMAGE | | TRANSMISSION ANGLE | NUMBER OF TRANSMISSION | FOCUSED BEAM IMAGE |
| 1 | 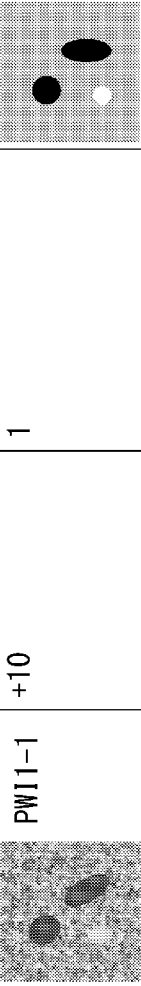 | PWI1-1 | +10 | 1 | 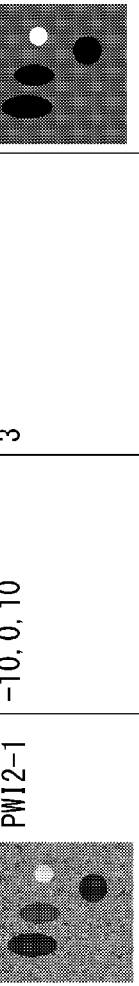 FB1 |
| 2 |  | PWI1-2 | ±0 | 1 | 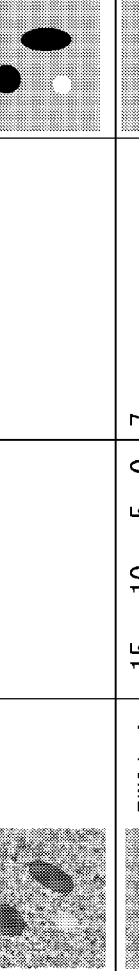 FB1 |
| 3 | 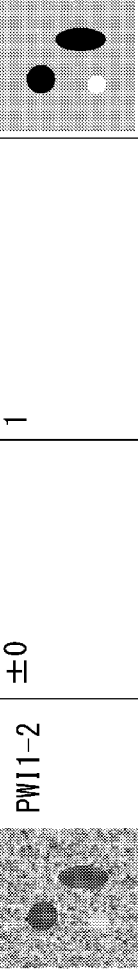 | PWI1-3 | -10 | 1 |  FB1 |
| 4 | 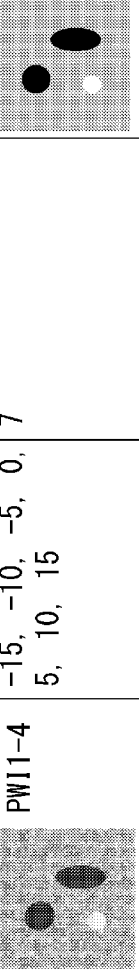 | PWI1-4 | -15, -10, -5, 0, 5, 10, 15 | 7 | 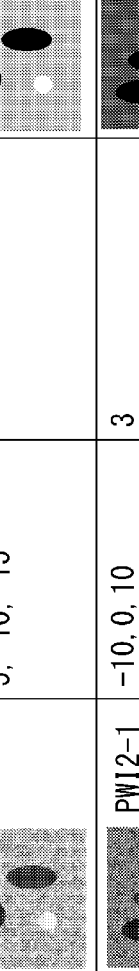 FB1 |
| 5 | 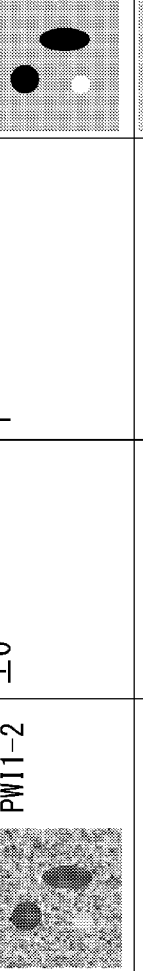 | PWI2-1 | -10, 0, 10 | 3 |  FB2 |

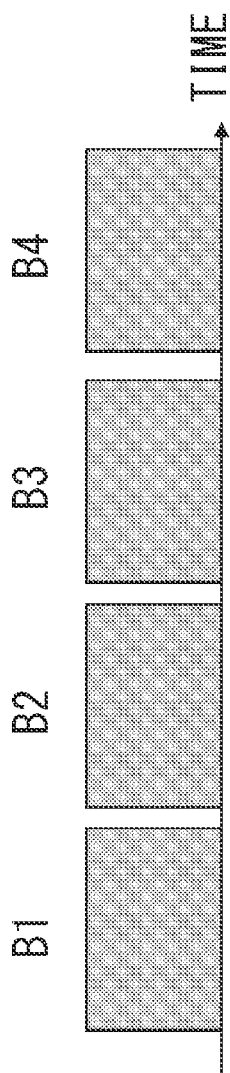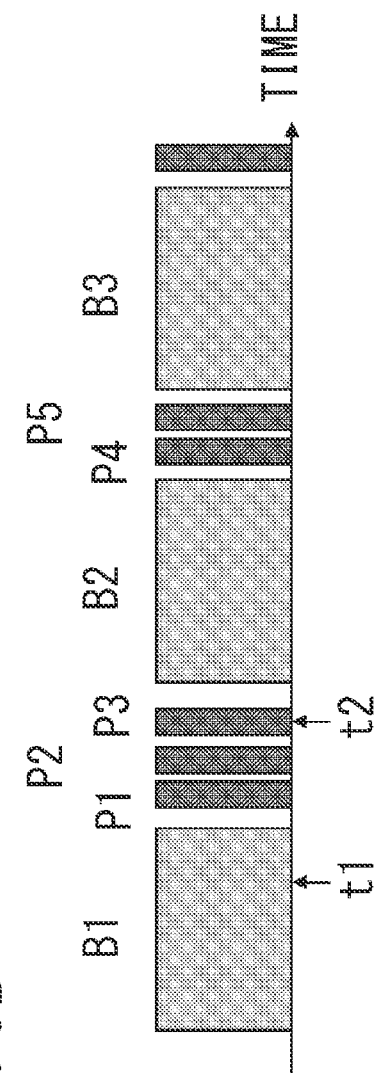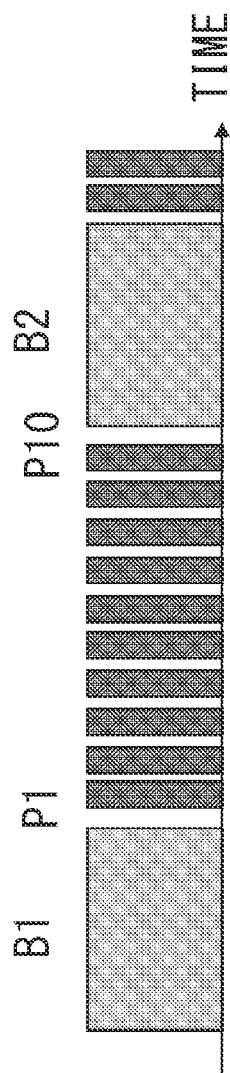

ULTRASONIC DIAGNOSTIC APPARATUS, LEARNING APPARATUS, AND IMAGE PROCESSING METHOD

BACKGROUND

Field of the Disclosure

The present disclosure relates to an ultrasonic diagnostic apparatus, a learning apparatus, an image processing method, and a program and, in particular, to a technique for improving image quality of an ultrasonic image.

Description of the Related Art

Ultrasonic diagnostic apparatuses are widely used in clinical practice as image diagnostic apparatuses due to, for example, simplicity, high resolution performance, and real-time performance thereof. As a method of image formation of such ultrasonic diagnostic apparatuses, a method of generating an image by beamforming processing of a transmit beam and phasing addition processing of a received signal is commonly used. Beamforming of a transmit beam is achieved by inputting a voltage waveform provided with a time delay relative to a plurality of conversion elements and causing ultrasonic waves to converge inside a living organism. In addition, phasing addition of a received signal is achieved by receiving ultrasonic waves reflected by a structure inside a living organism by a plurality of conversion elements, and providing to obtained received voltage signals a time delay in consideration of a path length with respect to a point of interest, and then adding up the received voltage signals. Due to the beamforming processing of the transmit beam and the phasing addition processing, reflected signals from the point of interest are selectively extracted to perform imaging. In addition, by controlling the transmit beam so that the inside of an imaging region is scanned by the transmit beam, it is possible to obtain an image of a region desired to be observed.

In addition, a method called plane wave transmission is sometimes used as an image generation method. In this method, beamforming of a transmit beam is hardly performed and ultrasonic waves are transmitted by a voltage waveform provided with a time delay so as to form an approximate plane wave or a diffuse wave. In addition, imaging is performed by subjecting reflected waves from a plane wave or a diffuse wave, transmitted in a plurality of directions or transmitted a plurality of times regarding a received signal, to phasing addition (aperture synthesis).

In image generation by plane wave transmission, since reflected waves over a wider range can be obtained by one transmission of a plane wave as compared to the transmit beam described above, in a case of imaging a region with a same size, a received signal can be obtained by a smaller number of transmissions/receptions by using a plane wave than by using a transmit beam. In other words, image generation by plane wave transmission enables imaging to be performed at a higher frame rate.

Japanese Patent Application Laid-open No. 2009-219876 discloses an ultrasonic diagnostic apparatus using a plane wave. Japanese Patent Application Laid-open No. 2019-25044 discloses a medical imaging apparatus using a restorer constituted by a neural network.

In addition, Maxime Gasse, et al., "High-Quality Plane Wave Compounding Using Convolutional Neural Networks," in IEEE Transactions on Ultrasonics Ferroelectrics and Frequency Control PP (99):1-1, August 2017 describes imaging using plane wave transmission and convolutional neural networks.

SUMMARY

Compared to focused transmission of ultrasonic waves, with plane wave transmission of ultrasonic waves, since a region for the ultrasonic wave transmission cannot be set, a ratio of reflected signals from other to the point of interest mixed in an image increases.

Therefore, there is a problem in that an image acquired using plane wave transmission of ultrasonic waves has a lower image quality than an image acquired using focused transmission of ultrasonic waves.

The present disclosure has been made in consideration of the problem described above and an object thereof is to provide an ultrasonic diagnostic apparatus that enables an image with favorable image quality to be obtained while realizing a high frame rate.

According to an aspect, it is provided an ultrasonic diagnostic apparatus including an ultrasonic probe configured to transmit and receives ultrasonic waves to and from an observation region of an object, and an estimated image generating unit configured to generate estimated image data corresponding to image data based on an ultrasonic focused beam from image data obtained by transmission of an ultrasonic plane-wave beam by using a model having been machine-learned from learning data including image data obtained by the transmission of the ultrasonic plane-wave beam and image data obtained by the transmission of the ultrasonic focused beam.

According to another aspect, it is provided a learning apparatus including a learning unit configured to perform machine learning of a model by using learning data that includes image data, obtained by transmission of an ultrasonic plane-wave beam, as input data and image data, obtained by transmission of an ultrasonic focused beam, as ground truth data.

According to another aspect, it is provided an image processing method including transmitting and receiving ultrasonic waves to and from an observation region of an object by an ultrasonic probe, and generating estimated image data corresponding to image data based on an ultrasonic focused beam from image data obtained by transmission of an ultrasonic plane-wave beam by using a model having been machine-learned from learning data including image data obtained by the transmission of the ultrasonic plane-wave beam and image data obtained by the transmission of the ultrasonic focused beam.

According to another aspect, it is provided a non-transitory computer readable medium storing a program causing a computer to execute the image processing method as described above.

Further features of the present invention will become apparent from the following description of exemplary embodiments with reference to the attached drawings.

BRIEF DESCRIPTION OF THE DRAWINGS

FIG. 4 is a diagram showing an example of learning data using a plane-wave beam image and a focused beam image;

FIGS. 9A to 9C are diagrams representing a time sequence according to the second embodiment;

DESCRIPTION OF THE EMBODIMENTS

First Embodiment

Configuration of Ultrasonic Diagnostic Apparatus

Figure 1:
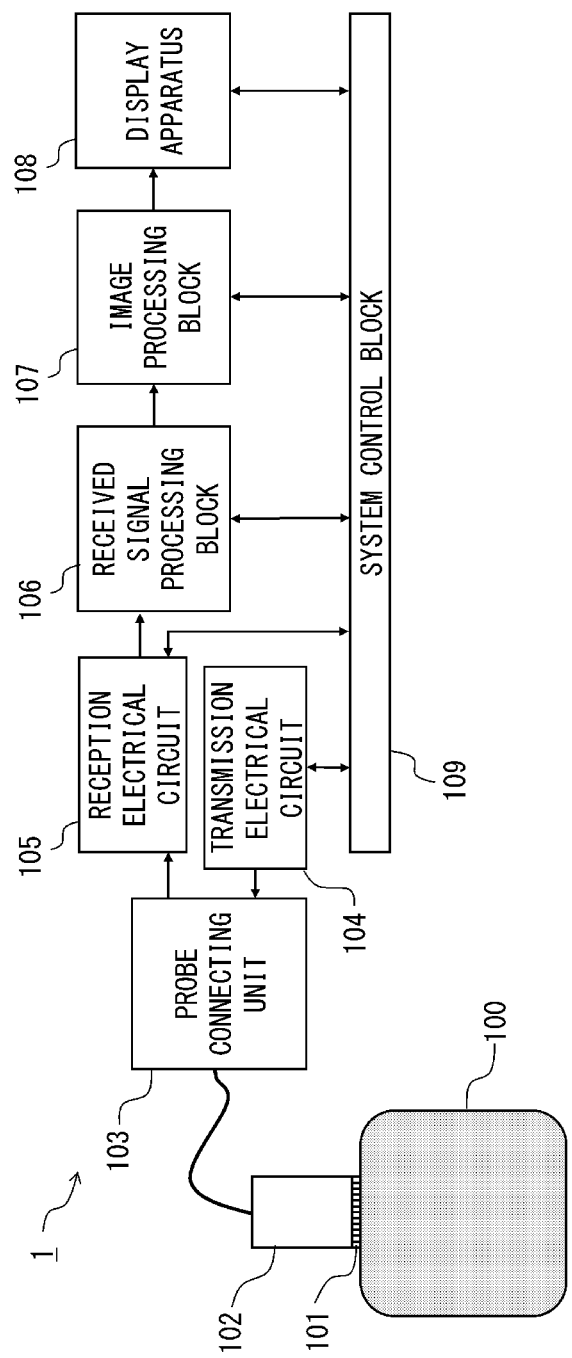
FIG. 1 is a block diagram showing an example of a hardware configuration of an ultrasonic diagnostic apparatus.

A first embodiment of the present invention will be described. FIG. 1 is a block diagram showing an example of a hardware configuration of an ultrasonic diagnostic apparatus. In general, an ultrasonic diagnostic apparatus 1 has an ultrasonic probe (an ultrasonic transducer) 102, a probe connecting unit 103, a transmission electrical circuit 104, a reception electrical circuit 105, a received signal processing block 106, an image processing block 107, a display apparatus 108, and a system control block 109. The ultrasonic diagnostic apparatus 1 is a system for transmitting an ultrasonic pulse to an object 100 from the ultrasonic probe 102, receiving reflected ultrasonic waves having been reflected inside the object 100, and generating image information (an ultrasonic image) of the inside of the object 100. The ultrasonic image obtained by the ultrasonic diagnostic apparatus 1 is to be used in various clinical examinations.

The ultrasonic probe 102 is a probe adopting an electronic scan system and has a plurality of transducers 101 arranged one-dimensionally or two-dimensionally at a tip thereof. The transducer 101 is an electric mechanical conversion element that performs mutual conversion between an electric signal (a voltage pulse signal) and an ultrasonic wave (an acoustic wave). The ultrasonic probe 102 transmits ultrasonic waves from the plurality of transducers 101 to the object 100 and receives reflected ultrasonic waves reflecting a difference in acoustic impedances inside the object 100 by the plurality of transducers 101.

The transmission electrical circuit 104 is a transmitting unit that outputs a pulse signal (a drive signal) with respect to the plurality of transducers 101. By applying a pulse signal with a time difference with respect to the plurality of transducers 101, ultrasonic waves with different delay times are transmitted from the plurality of transducers 101 and a transmission ultrasonic beam is formed. By selectively changing the transducer 101 to which the pulse signal is applied (in other words, the transducer 101 to be driven) and changing a delay time (application timing) of the pulse signal, a direction and a focus of the transmission ultrasonic beam can be controlled. An observation region inside the object 100 is scanned by sequentially changing the direction and the focus of the transmission ultrasonic beam. In the following description, among transmission ultrasonic beams formed by the transmission electrical circuit 104, a transmission ultrasonic beam of which a spread is at least a threshold that is approximately half of a transmission aperture size will be referred to as a plane-wave beam. A spread of a transmission ultrasonic wave refers to a beam width from a maximum sound pressure point to a sound pressure point at which sound pressure is approximately half of maximum sound pressure. In addition, among transmission ultrasonic beams formed by the transmission electrical circuit 104, a transmission ultrasonic beam of which a spread is smaller than the threshold of the transmission aperture size will be referred to as a focused beam.

The reception electrical circuit 105 is a receiving unit that inputs, as a received signal, an electric signal output from the transducer 101 having received a reflected ultrasonic wave. The received signal is input to the received signal processing block 106. Operations of the transmission electrical circuit 104 and the reception electrical circuit 105 or, in other words, transmission/reception of ultrasonic waves is controlled by the system control block 109. It should be noted that, in the present specification, both an analog signal output from the transducer 101 and digital data obtained by sampling (digitally converting) the analog signal will be referred to as a received signal without particular distinction. However, a received signal will sometimes be described as received data depending on the context in order to clearly indicate that the received signal is digital data.

The received signal processing block 106 generates image data based on a received signal obtained from the reception electrical circuit 105. The image processing block 107 applies image processing such as brightness adjustment, interpolation, and filter processing on the image data generated by the received signal processing block 106. The display apparatus 108 is a display unit for displaying image data and various kinds of information and is constituted by, for example, a liquid crystal display or an organic EL display. The system control block 109 is a control unit that integrally controls the transmission electrical circuit 104, the reception electrical circuit 105, the received signal processing block 106, the image processing block 107, the display apparatus 108, and the like.

Configuration of Received Signal Processing Block

Figure 2:
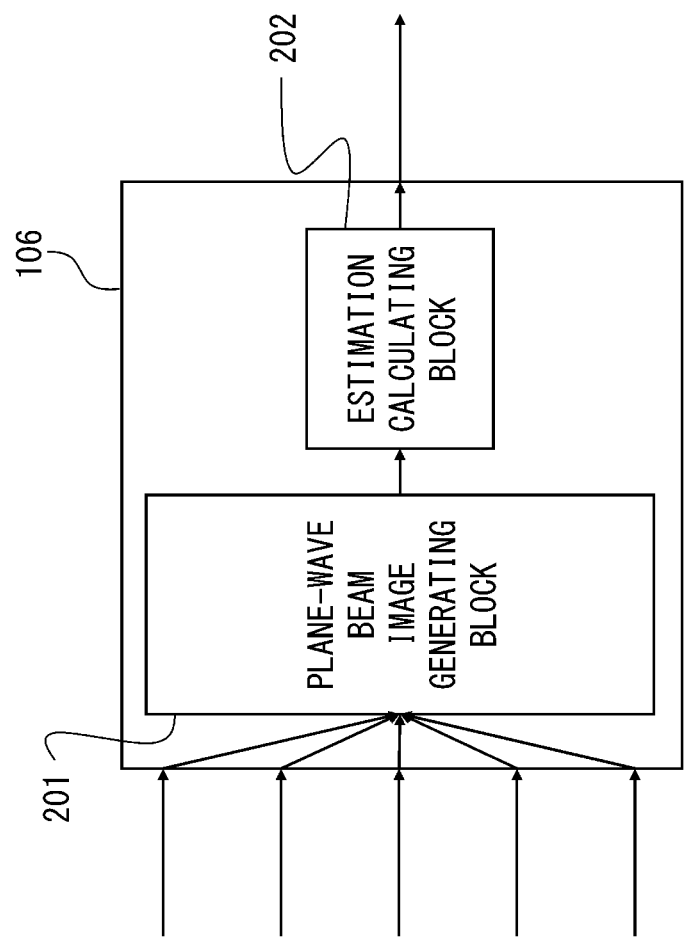
FIG. 2 is a block diagram showing details of a received signal processing block according to a first embodiment.

FIG. 2 is a block diagram showing an example of functions included in the received signal processing block 106. The received signal processing block 106 has a plane-wave beam image generating block 201 and an estimation calculating block 202. In the present embodiment, the plane-wave beam image generating block 201 (an image generating unit) generates focused beam image data that is obtained by transmitting a focused beam with an ultrasonic probe. In addition, using a model having been machine-learned using learning data including image data obtained by transmission of an ultrasonic plane-wave beam and image data obtained by transmission of an ultrasonic focused beam, the estimation calculating block 202 (an estimated image generating unit) generates estimated image data corresponding to image data based on an ultrasonic focused beam from image data obtained by the transmission of an ultrasonic plane-wave beam.

The plane-wave beam image generating block 201 generates an image from a received signal obtained from the reception electrical circuit 105 based an element arrangement and various conditions of image generation (sound velocity, aperture control, and signal filtering) supplied from the system control block 109. The image generated by the plane-wave beam image generating block 201 is sent to the estimation calculating block 202.

The estimation calculating block 202 generates a focused beam-equivalent image based on an image sent from the plane-wave beam image generating block 201 using a learned model having been obtained by machine learning. A "focused beam-equivalent image" refers to an image of which image quality has been improved to a level equivalent to that of an image (referred to as a focused beam image) obtained by transmitting a focused beam by applying image processing (estimation calculation processing) to a single plane-wave beam image. In the following description, a focused beam-equivalent image may also be referred to as an "estimated value". An image output from the estimation calculating block 202 is subjected to prescribed processing by the image processing block 107 and subsequently displayed by the display apparatus 108.

The received signal processing block 106 may be constituted by at least one processor and a memory. In this case, functions of the respective blocks 201 and 202 shown in FIG. 2 are to be realized by a computer program. For example, the functions of the respective blocks 201 and 202 can be provided by having a CPU load and execute a program stored in the memory. Other than the CPU, the received signal processing block 106 may include a processor (a GPU, an FPGA, or the like) responsible for operations of the respective blocks 201 and 202. In particular, an FPGA is effectively used in the plane-wave beam image generating block 201 to which a large amount of data is input at the same time and a GPU is effectively used when executing operations in an efficient manner as in the estimation calculating block 202. The memory favorably includes a memory for storing a program in a non-transitory manner, a memory for temporarily saving data such as a received signal, and a working memory to be used by the CPU.

Estimation Calculating Block

The estimation calculating block 202 will now be described. The estimation calculating block 202 performs processing for generating (estimating) a focused beam-equivalent image using a learned model.

Machine learning is favorably used to learn a model. Examples of a specific algorithm for machine learning include a nearest neighbor method, a naive Bayes method, and a support vector machine. Another example is deep learning that autonomously generates a feature amount and a coupling weight coefficient for learning using a neural network. A usable algorithm among those described above can be appropriately used and applied to the present embodiment.

Figure 3:
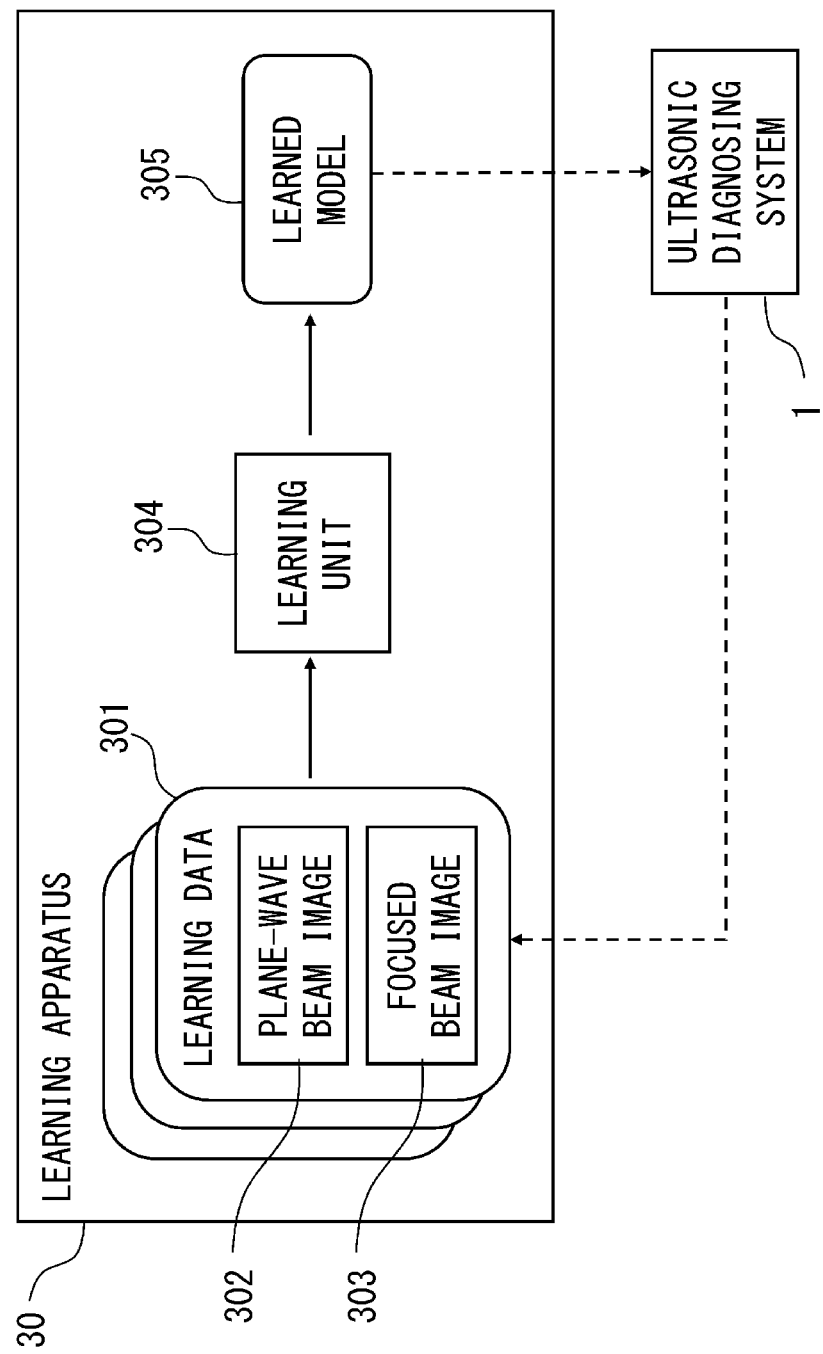
FIG. 3 is a block diagram showing an example of a learning apparatus.

FIG. 3 shows an example of a learning apparatus 30 that performs machine learning of a model. The learning apparatus 30 has a learning unit (a learner) 304 that carries out machine learning of a model using a plurality of pieces of learning data 301. The learning unit 304 may use any of the machine learning algorithms exemplified above or may use another machine learning algorithm. The learning data 301 is constituted by a pair of input data and ground truth data (teacher data) and, in the present embodiment, a plane-wave beam image 302 (image data obtained by transmission of a plane-wave beam) is used as the input data. In addition, a focused beam image 303 (image data obtained by transmission of a focused beam) is used as the ground truth data. Furthermore, the plane-wave beam image 302 and/or the focused beam image 303 may include radio frequency (RF) data (raw data). The learning unit 304 learns a correlation between the plane-wave beam image 302 and the focused beam image 303 based on the plurality of pieces of supplied learning data 301 and creates a learned model 305. Accordingly, the learned model 305 can acquire a function (a capability) of generating a focused beam-equivalent image as output data when a plane-wave beam image is given as input data. The learned model 305 is mounted to a program to be executed by the estimation calculating block 202 of the ultrasonic diagnostic apparatus 1. Learning of a model (generation processing of the learned model 305) is desirably performed before being incorporated into the ultrasonic diagnostic apparatus 1. However, when the ultrasonic diagnostic apparatus 1 has a learning function, learning (new learning or additional learning) may be performed using image data obtained by the ultrasonic diagnostic apparatus 1.

FIG. 4 is a diagram explaining learning by the estimation calculating block 202 that outputs a plane-wave beam image. In the learning, a plane-wave beam image obtained by imaging an object with a plane-wave beam, or a transmission angle and/or the number of transmissions of the plane-wave beam is used as input. In addition, a focused beam image obtained by imaging the same object using a focused beam is used as ground truth data.

Learning by the estimation calculating block 202 according to the present embodiment will now be described in greater detail. As shown in FIG. 4, a plane-wave beam image PWI1-1 is used as input data of learning data ID1. In addition, a representative angle of transmission directions (a transmission angle) of a plane-wave beam with respect to a direction perpendicular to a probe surface, the number of transmissions of the plane-wave beam, and the like in transmissions of the plane-wave beam for obtaining a received signal on which the image is to be based are also included in the input data. In the example shown in FIG. 4, the number of transmissions of the plane-wave beam when acquiring the plane-wave beam image PWI1-1 is one at +10 degrees. Furthermore, as ground truth data of the learning data ID1, a focused beam image FB1 obtained by transmitting a focused beam to the same object is used. In a similar manner, as pieces of input data of the pieces of learning data ID2 to ID4, sets of plane-wave beam images PWI1-2 to 1-4 and a representative angle of transmission directions, the number of transmissions, and the like of a plane-wave beam are used. Furthermore, as ground truth data of the pieces of learning data ID2 to ID4, the focused beam image FB1 is used. Therefore, learning is performed by using, as ground truth data, the focused beam image FB1 obtained by transmitting a focused beam with respect to the plane-wave beam images PWI1-1 to 1-4 that are obtained by transmitting a plane-wave beam under different conditions with respect to the same object.

Furthermore, as input data of learning data ID5, a plane-wave beam image PWI2-1 obtained by transmitting a plane-wave beam to an object that differs from the object that is an imaging object of the plane-wave beam image PWI1-1 is used. In addition, as ground truth data of the learning data ID5, a focused beam image FB2 obtained by transmitting a focused beam to a same object as the object of the plane-wave beam image PWI2-1 is used. It should be noted that the plane-wave beam image input to the estimation calculating block 202 may be image data obtained using a signal that combines a plurality of received signals respectively obtained by a plurality of transmissions of the plane-wave beam. As described above, in the present embodiment, learning is performed by using a set of a plane-wave beam image and a focused beam image obtained by transmitting a plane-wave beam under different conditions with respect to different objects.

As shown in FIG. 4, learning is favorably performed using various pieces of learning data such as learning data representing different transmission conditions of the plane-wave beam and learning data representing different objects.

Performing learning using as many pieces of learning data as possible enables learning to be performed with respect to input data of various patterns, and an image with good image quality can be expected to be estimated even during actual use. It should be noted that, as an object, any of a digital phantom that can be imaged by a transmission/reception simulation of ultrasonic waves, an actual phantom, and an actual living organism may be used.

In addition, preprocessing of learning data may be performed. For example, learning efficiency may be improved by correcting non-uniformity of brightness values due to attenuation of ultrasonic waves. Even in a focused beam image, an image of a portion where an ultrasonic beam converges in a favorable manner or, in other words, a vicinity of a depth at which a transmission focus has been set may be extracted and used. Accordingly, an improvement in resolution of an estimated image can be expected. Processing for removing a shadow caused by a separation of an ultrasonic probe during imaging of an object or the like from input data may be performed. Accordingly, stability of estimation accuracy can be improved. Alternatively, by using learning data in which both input data and ground truth data include a shadow caused by a separation of an ultrasonic probe or the like, an effect can be expected that an image enabling separation of the probe to be recognized be estimated by an estimated image when a separation of a probe actually occurs.

Figure 5:
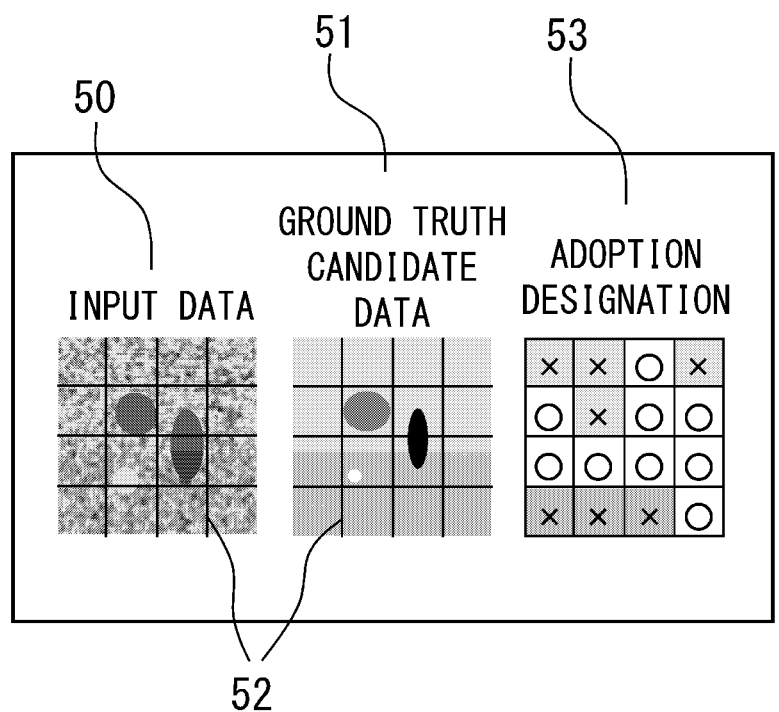
FIG. 5 is a diagram showing an example of a GUI for creating learning data.

In addition, in learning, preprocessing of input data and ground truth data may be further performed using a GUI such as that shown in FIG. 5. Input data 50 and ground truth candidate data 51 are shown in a display screen, and indicators 52 that divide each piece of data into a plurality of regions are displayed. In the example shown in FIG. 5, images are divided into 16 regions in a 4 by 4 arrangement. An adoption designation box 53 is a user interface that enables a user to designate whether to adopt or reject each region. The user enters "○" into a region to be adopted as learning data and "x" into a region to be excluded while comparing the input data 50 and the ground truth candidate data 51 with each other. Accordingly, locations where unexpected image deterioration has occurred in the ground truth candidate data 51 and the like can be excluded. For example, a location where it is determined that image quality has declined due to movement of an object while a transmission ultrasonic beam had been transmitted and received a plurality of times and the like can be excluded. While FIG. 4 has been described on the assumption that an entire image is to be used as one piece of image data, when an image is divided into a plurality of regions as shown in FIG. 5, an image (a partial image) of each of the regions is used as one piece of learning data. In other words, in the example shown in FIG. 5, since there are 9 regions to be adopted, 9 sets of learning data are to be generated.

While a plane-wave beam image and a transmission angle and/or the number of transmissions of a plane-wave beam are exemplified as input data in the present embodiment, a similar advantageous effect to that of the present embodiment can be obtained even when only a plane-wave beam image is used as input data. In addition, related information other than a plane-wave beam image and a transmission angle and/or the number of transmissions of a plane-wave beam may be added to input data. For example, adding information such as a transmission frequency and a band of a bandpass filter when acquiring a plane-wave beam image to input data increases the possibility that accurate estimation can be performed in accordance with a state of the input data. In addition, information describing which portion of a living organism the object represents, which orientation the ultrasonic probe is in contact relative to a body axis, and the like may be added to input data. It is expected that estimation accuracy will further increase in correspondence to a feature of each site (for example, the presence of a surface fat layer, the presence of a high brightness region created by a fascial structure, or the presence of a low brightness region due to a thick blood vessel). Furthermore, by adding information such as a field of medicine, gender, BMI, age, and pathological condition to input data, there is a possibility that a learned model corresponding to the feature of each site described earlier in greater detail can be obtained and a further increase in estimation accuracy is expected.

In addition, the learned model 305 of the estimation calculating block 202 mounted to the ultrasonic diagnostic apparatus 1 may be a model having learned image data of all fields of medicine or a model having learned image data of each field of medicine. When a model having learned image data of each field of medicine is mounted, the system control block 109 may cause the user of the ultrasonic diagnostic apparatus 1 to input or select information regarding a field of medicine to change the learned model to be used in accordance with the field of medicine. It is expected that estimation accuracy will further increase by selectively using a model for each field of medicine in which imaging sites are limited to a certain degree.

The learned model 305 obtained by performing learning using a variety of such imaging conditions and a plane-wave beam image as input data and a focused beam image as ground truth data operates on the estimation calculating block 202. As a result, it is expected that the estimation calculating block 202 will estimate an image corresponding to a focused beam image with high resolution or contrast with respect the input plane-wave beam image and output the estimated image as an estimation result.

Image Generation Method

Next, details of processing for image generation according to the present embodiment will be described with reference to FIG. 1. An imaging instruction is input by the user using a GUI (not illustrated). The system control block 109 having received the instruction from the GUI inputs a transmission instruction of ultrasonic waves to the transmission electrical circuit 104. The transmission instruction favorably includes a parameter for calculating a delay time and sound velocity information. Based on the transmission instruction from the system control block 109, the transmission electrical circuit 104 outputs a plurality of pulse signals (voltage waveforms) to the plurality of transducers 101 of the ultrasonic probe 102 through the probe connecting unit 103. At this point, the transmission electrical circuit 104 sets a delay time of a pulse signal to be applied to each transducer 101 in accordance with a transmission direction (a deflection angle) and a focus position of the ultrasonic beam. In this case, a deflection angle is an angle formed between a normal direction of a surface on which the plurality of transducers 101 are arranged and an axial direction of the ultrasonic beam.

The ultrasonic waves transmitted from the plurality of transducers 101 propagate inside the object 100 and are reflected at a boundary of acoustic impedance inside the object 100. The plurality of transducers 101 receive reflected ultrasonic waves that reflect a difference in acoustic impedances and convert the reflected ultrasonic wave into a voltage waveform. The voltage waveform is input to the reception electrical circuit 105 through the probe connecting unit 103. The reception electrical circuit 105 amplifies and digitally samples the voltage waveform as necessary and outputs the voltage waveform as a received signal to the received signal processing block 106.

Figure 6:
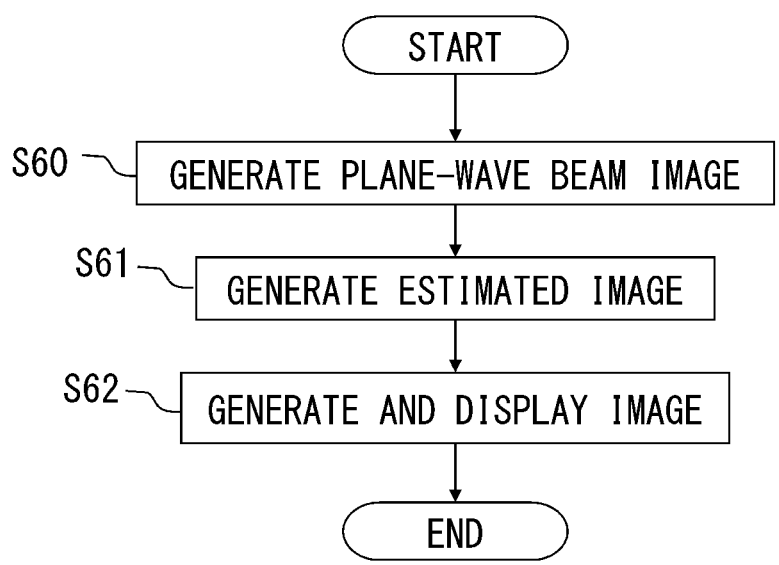
FIG. 6 is a diagram representing a flow of processing according to the first embodiment.

FIG. 6 shows a flow of image generation and display processing executed by each block of the ultrasonic diagnostic apparatus 1 in the present embodiment. In step S60, the plane-wave beam image generating block 201 generates a plane-wave beam image based on a received signal obtained by the reception electrical circuit 105 and an element arrangement and various conditions of image generation input from the system control block 109. In this case, various conditions include a sound velocity, an element pitch, a bandpass band, and a receiving aperture size. The plane-wave beam image generating block 201 outputs the generated plane-wave beam image to the estimation calculating block 202.

In step S61, the estimation calculating block 202 executes an estimation calculation using a transmission angle, the number of transmissions, and the like of the plane-wave beam input from the system control block 109 and outputs a focused beam-equivalent image (an estimated image).

The plane-wave beam image input to the estimation calculating block 202 may be an image created by a signal obtained by combining a plurality of received signals respectively obtained by a plurality of transmissions of the plane-wave beam. When creating an image based on a result of a plurality of plane-wave beam transmissions in this manner, the plane-wave beam image output from the plane-wave beam image generating block 201 is saved in a memory. In addition, a plurality of subsequently output plane-wave beam images and the image saved in the memory are combined with each other and a combination result thereof is output together with a plurality of transmission angles to the estimation calculating block 202. The combining of plane-wave beam images may be either coherent or incoherent, and the advantageous effect of the present embodiment is obtained as long as a plane-wave beam image as a result of using the combining method is used as input data during learning.

In step S62, data of the estimated image output from the estimation calculating block 202 is input to the image processing block 107. The image processing block 107 applies brightness adjustment, interpolation, and other filtering with respect to the input data of the estimated image and outputs image data obtained as a result thereof to the display apparatus 108. The display apparatus 108 displays the image data output from the image processing block 107 and the ultrasonic diagnostic apparatus 1 ends processing of the present flow.

Figure 7A:
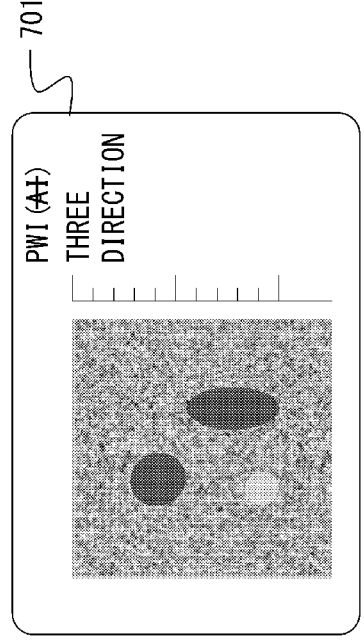
FIGS. 7A to 7C are diagrams representing an example of display by a display apparatus according to the first embodiment.
Figure 7B:
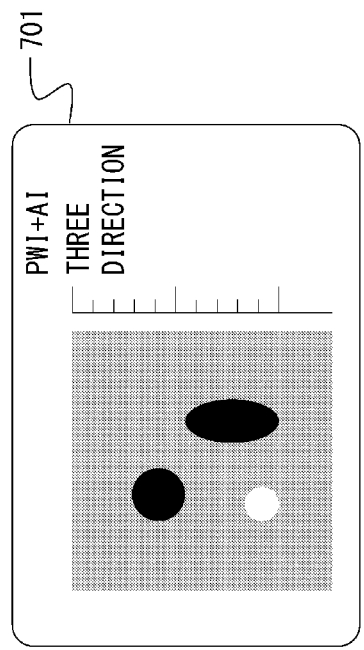
Figure 7C:
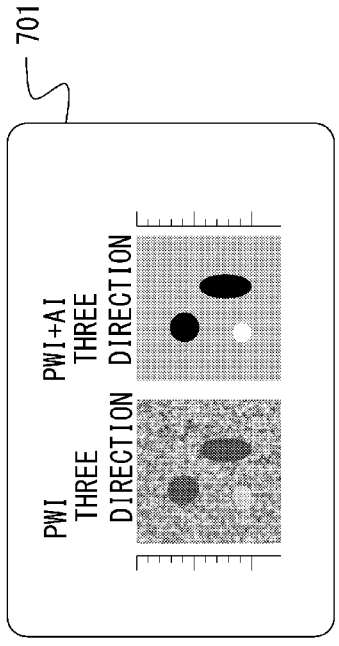

FIGS. 7A to 7C schematically show a display example of an image on the display apparatus 108. FIG. 7A shows a state where the estimated image output from the estimation calculating block 202 is displayed in a display region 701 of the display apparatus 108. Since the estimated image output from the estimation calculating block 202 is not an image created by directly imaging received ultrasonic waves but includes estimation, the fact that the image is estimated is displayed in the display region 701. In the example shown in FIG. 7A, "PWI+AI" indicating that the image is an estimated image is displayed. In addition, it is also displayed in the display region 701 that representative features of an image to be a basis of estimation are three directions that represent imaging conditions (the image input to the estimation calculating block 202 is a plane-wave beam image obtained by transmitting a plane-wave beam in three directions). It should be noted that these displays need not be displays by characters and, for example, methods such as changing a color of an outer edge of a display image or a display region, causing the outer edge to blink, and changing a color, chroma, or a pattern of a background of the display image or the display region may be adopted.

FIG. 7B shows a state where the image obtained by transmitting a plane-wave beam is displayed as-is in the display region 701 without operating the estimation calculating block 202. The exemplary image shown in FIG. 7B is obtained by outputting, as-is to the image processing block 107, the plane-wave beam image having been output by the plane-wave beam image generating block 201 of the received signal processing block 106. In addition, since a plane-wave beam transmission is performed, an image being displayed in the display region 701 can be switched at an arbitrary timing to an estimated image output by the estimation calculating block 202. In the example shown in FIG. 7B, "PWI (AI)" (a strike-through line is drawn through "AI") is displayed which indicates that, while it is possible to switch to the estimated image output by the estimation calculating block 202, the estimated image is currently not in use.

FIG. 7C shows a state where the plane-wave beam image output by the plane-wave beam image generating block 201 and the estimated image output by the estimation calculating block 202 are displayed side by side in the display region 701. In the example shown in FIG. 7C, two types of images are generated from received signals acquired at the same time due to plane-wave beam transmission. Accordingly, since the user can not only confirm an estimated image with improved image quality having been created by the estimation calculating block 202 but also confirm an original plane-wave beam image at the same time, an image unit that has been changed from the plane-wave beam image by processing of the estimation calculating block 202 can be recognized.

According to the present embodiment, an image can be provided based on high-speed data acquisition over a wide range by collecting received data due to plane-wave beam transmission or, in other words, an image can be provided at a higher frame rate than in a case of focused beam transmission. Furthermore, an image with a high image quality that resembles image quality of an image obtained by focused beam transmission can be provided through learning of the estimation calculating block 202. Therefore, the ultrasonic diagnostic apparatus 1 is capable of providing an image with a higher frame rate and higher contrast than conventional apparatuses.

Second Embodiment

Next, an ultrasonic diagnostic apparatus according to a second embodiment will be described. An overall configuration of the ultrasonic diagnostic apparatus 1 is the same as that of the first embodiment (FIG. 1). In the present embodiment, a plane-wave beam and a focused beam are used as ultrasonic beams to be transmitted. A received voltage signal is obtained by transmitting a plane-wave beam and the received voltage signal is input to the received signal processing block 106 in a similar manner to the first embodiment. In addition, in the present embodiment, acquisition of a received voltage signal due to transmission of a focused beam is also performed. In accordance with an instruction from the system control block 109, the transmission electrical circuit 104 supplies a voltage signal imparted with a delay so as to converge inside an object to the transducers 101 of the ultrasonic probe 102 through the probe connecting unit 103. The ultrasonic probe 102 repeats transmission/reception by a focused beam while moving positions or, in other words, while scanning so that the focused beam is transmitted across an entire imaging region. Therefore, compared to transmission of a plane-wave beam, an imaging region that can be imaged per unit time is narrower in the case of transmission of a focused beam.

Figure 8:
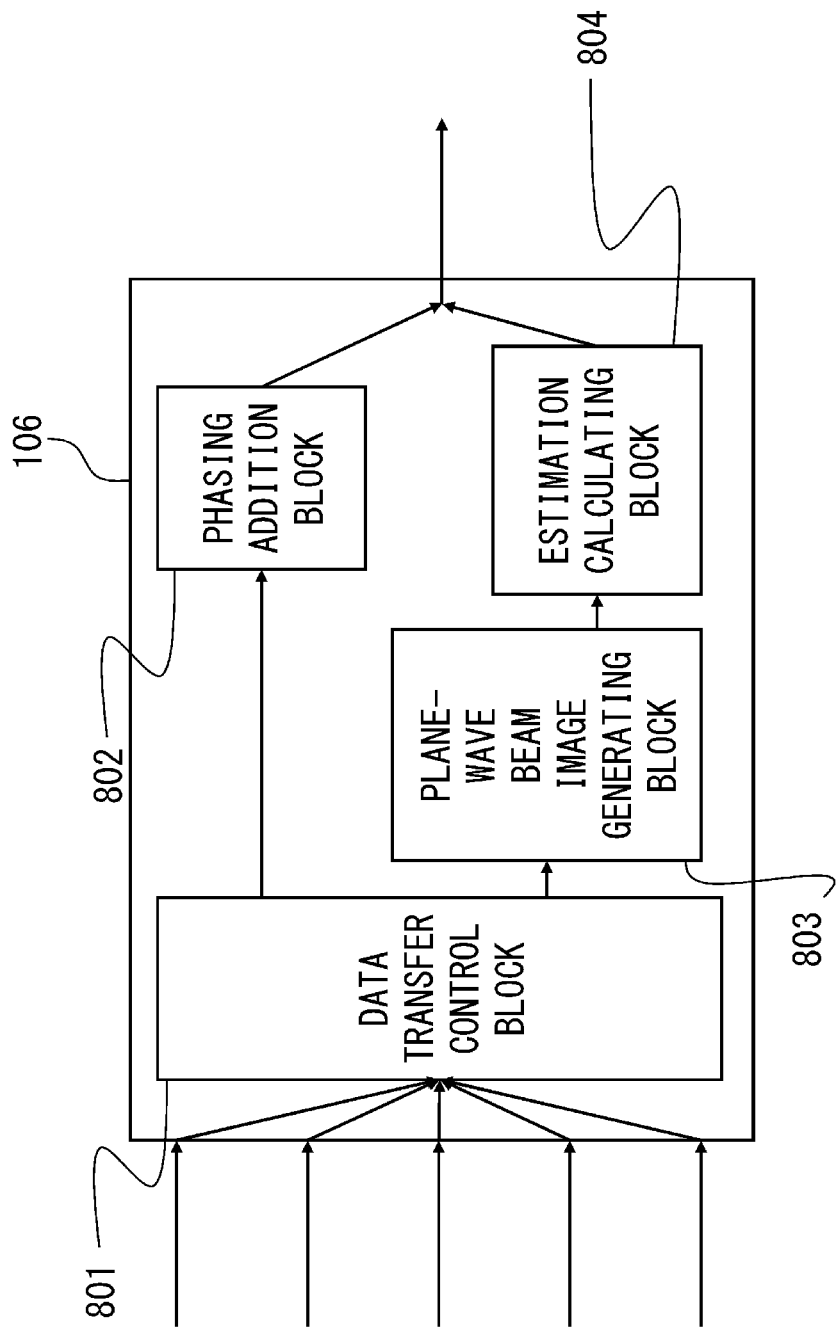
FIG. 8 is a block diagram showing details of a received signal processing block according to a second embodiment.

FIG. 8 shows the received signal processing block 106 according to the present embodiment. The received signal processing block 106 has a data transfer control block 801, a phasing addition block 802, a plane-wave beam image generating block 803, and an estimation calculating block 804. In accordance with information from the system control block 109, the data transfer control block 801 determines whether a received signal is due to a focused beam or a plane-wave beam and changes a data transfer destination. When the received signal is due to a focused beam, the data transfer control block 801 transfers received data to the phasing addition block 802. On the other hand, when the received signal is due to a plane-wave beam, the data transfer control block 801 transfers received data to the plane-wave beam image generating block 803. The phasing addition block 802 and the plane-wave beam image generating block 803 respectively execute processing for generating an image with respect to the input received data. In addition, the estimation calculating block 804 generates an image according to the learned calculation described above using, as input, the plane-wave beam image from the plane-wave beam image generating block 803 and information such as a transmission angle of the plane-wave beam from the system control block 109.

Figure 10:
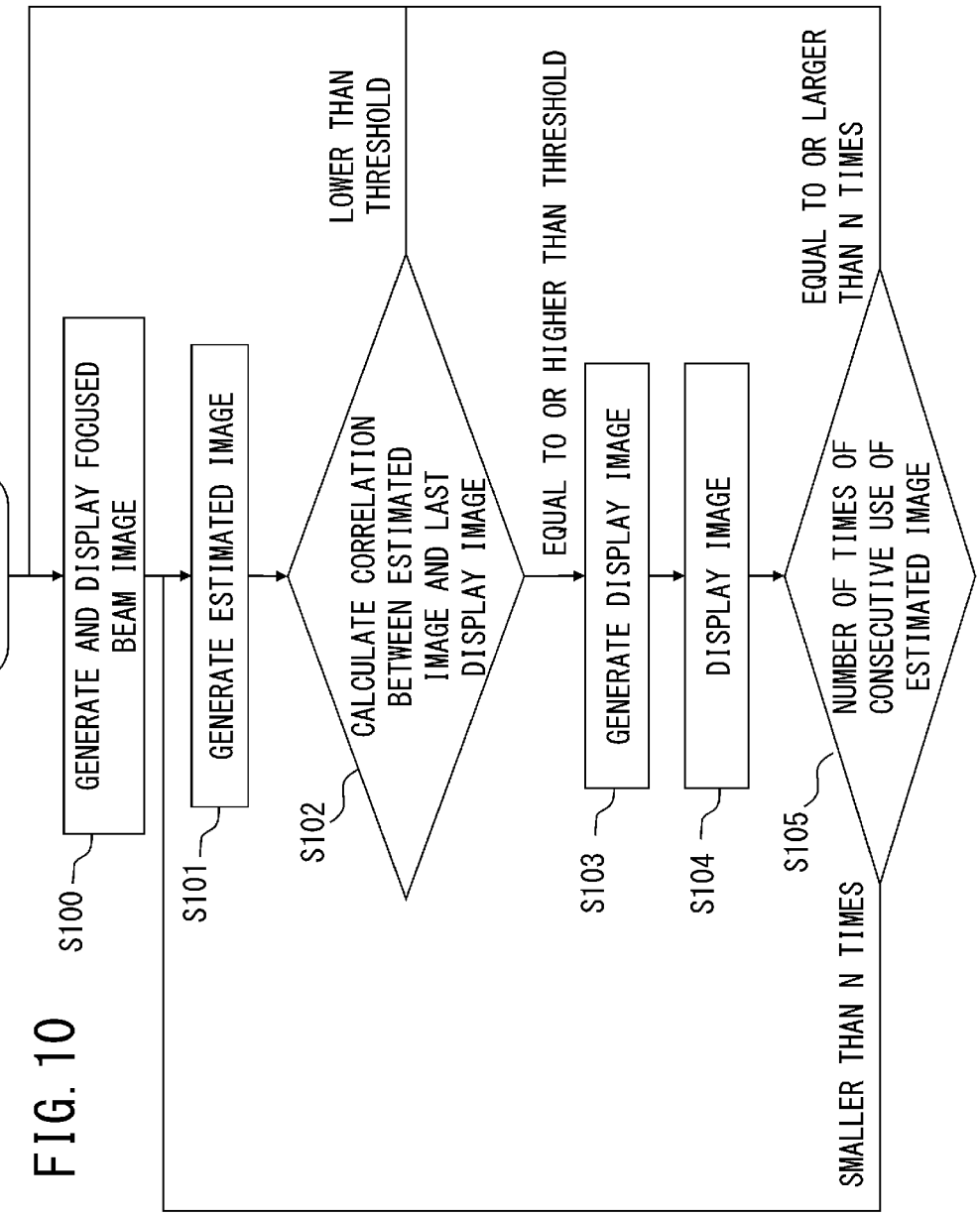
FIG. 10 is a diagram representing a flow of processing according to the second embodiment.

FIGS. 9A to 9C show an example of timings of formation of an estimated image and formation of a focused beam image from the plane-wave beam image in the estimation calculating block 804. FIG. 9A represents an example of a display mode in which a display image is updated using only the focused beam image and FIGS. 9B and 9C represent an example of a display mode in which a display image is updated using both the focused beam image and the estimated image. In addition, FIG. 10 is a flow chart showing an example of switching processing between formation of an estimated image and formation of a focused beam image in the display mode shown in FIGS. 9B and 9C.

FIGS. 9A to 9C are diagrams showing timings of phasing addition due to focused beam transmission and image formation due to plane-wave beam transmission. FIG. 9A exemplifies timings when an image is generated by focused beam transmission. Times required until an image (a frame) is output during a single scan by a focused beam across the imaging region are denoted by B1, B2, B3, and B4. In this case, four focused beam images are to be output.

Hereinafter, a description will be given with reference to the flow chart shown in FIG. 10. The apparatus is switched to a control mode shown in the flow chart according to an instruction from the user, a default setting of the apparatus, or a field of medicine or a user ID. It should be noted that the processing shown in FIG. 10 is realized as the respective units 101 to 108 of the ultrasonic diagnostic apparatus 1 operate under control of the system control block 109.

In step S100, a focused beam image is generated and displayed. Specifically, an observation region is scanned by a focused beam, a frame's worth of an entire image is generated, and the generated image is displayed on the display apparatus 108. A time required by the operation is denoted by B1 in FIG. 9B. It should be noted that the system control block 109 has a frame memory and is capable of temporarily saving display image data that is output from the received signal processing block 106.

In step S101, an estimated image is generated by performing processing by the plane-wave beam image generating block 803 and the estimation calculating block 804 with respect to a signal received due to transmission of a plane-wave beam. A time required by the operation is denoted by P1 in FIG. 9B.

In step S102, the system control block 109 evaluates whether or not the estimated image generated by the estimation calculating block 804 satisfies a prescribed condition. A purpose of the evaluation is to determine whether or not reliability of the estimated image (accuracy of estimation) is high and, in the present embodiment, it is determined that the higher a correlation with a last focused beam image stored in the frame memory, the higher the reliability. Metrics for evaluating correlation may be designed in any way. In the example shown in FIG. 9B, a correlation between each of the plane-wave beam images generated at times P1, P2, and P3 and the focused beam image generated at time B1 is evaluated. In the present embodiment, for example, a correlation strength is evaluated using an inverse of an SSD (a sum of squares of a difference in pixel values) between the estimated image and a last display image. When the correlation is at least a prescribed threshold or, in other words, when the estimated image has not changed significantly from the last focused beam image, validity or reliability of the estimated image is considered to be high. In addition, in step S103, the system control block 109 updates the display image using the estimated image. For example, the system control block 109 may generate a new display image by combining the last focused beam image and the present estimated image with a prescribed weight. Alternatively, the system control block 109 may adopt the present estimated image as the new display image as-is (it can be considered that a weight of the last focused beam image is 0 and a weight of the estimated image is 1). In step S104, the display image generated in step S103 is displayed on the display apparatus 108.

In step S105, the system control block 109 checks whether or not the number of times the estimated image was consecutively used to update the display image has reached a prescribed number of times N (in the present example, it is assumed that N=10). When the number of times is smaller than N, a return is made to step S101 and an estimated image using the plane-wave beam image is generated (B2 in FIG. 9B denotes a time required by this operation). Subsequently, processing of steps S102 to S105 is repeated.

When the correlation between the estimated image and the last display image falls below the prescribed threshold while the processing is being repeated, the system control block 109 does not use the estimated image for display and switches control to generating and displaying a new focused beam image (step S100). FIG. 9B represents an example in which, since the estimated image obtained at time P3 had a low correlation with the last focused beam image, a new focused beam image has been generated at time B2. Once a focused beam image is displayed, a switch is made to control for once again generating an estimated image (P4 and P5 in FIG. 9B each denotes a time required by this operation) (step S101).

In addition, in step S105, when it is determined that the number of times the estimated image was consecutively used to update the display image has reached N times, the system control block 109 stops generation of the estimated image and switches control to generating and displaying a new focused beam image (step S100). FIG. 9C represents an example in which, since the number of times the estimated image was consecutively used has reached 10 times (P1 to P10), a new focused beam image has been generated at time B2.

According to the control described above, since an estimated image generated from a focused beam image obtained in one scan is used to update a display image, image display can be realized at a higher frame rate than when updating the display image using only the focused beam image. As is apparent from a comparison between FIG. 9A (a display mode in which only a focused beam image is used) and FIG. 9B (a display mode in which both a focused beam image and an estimated image are used), it is shown that a larger number of frames can be displayed per unit time in the latter case. In addition, in the present embodiment, since control to switch to generating and displaying a focused beam image is performed when reliability of an estimated image declines, the possibility of displaying an image with low image quality or an image that represents a failed estimation can be suppressed. Furthermore, in the present embodiment, since processing for using an estimated image to update a last focused beam image or a last display image is performed instead of using the estimated image itself for display, image display with high reliability as a whole can be continued.

When calculating a correlation, a correlation between entire observation regions need not be used and a determination may be made based on, after dividing an observation region and calculating respective correlations of the divided regions, whether or not a correlation is at least a certain level in a certain percentage of the divided regions. By performing such control, for example, when imaging a heart, since a correlation of other regions remain high even though a correlation of a region containing a moving valve declines, display at a high frame rate using an estimated image can be continued.

In addition, while an image used to evaluate a correlation and an image used for display are the same in the processing shown in FIG. 10, different images may be used between evaluation of a correlation and display. For example, only an image in a partial region (referred to as a selected region) among the observation region may be used to evaluate a correlation, and generation of an image of the entire observation region may be controlled according to the evaluation by the image in the selected region. Accordingly, efficiency of imaging and image processing can be improved. It should be noted that the selected region may be arbitrarily set and, for example, a region constituting 1/n (where n is an integer of at least 2) of the observation region or a central region of the observation region may be mechanically set as the selected region or the user may be enabled to set the selected region.

Figure 11:
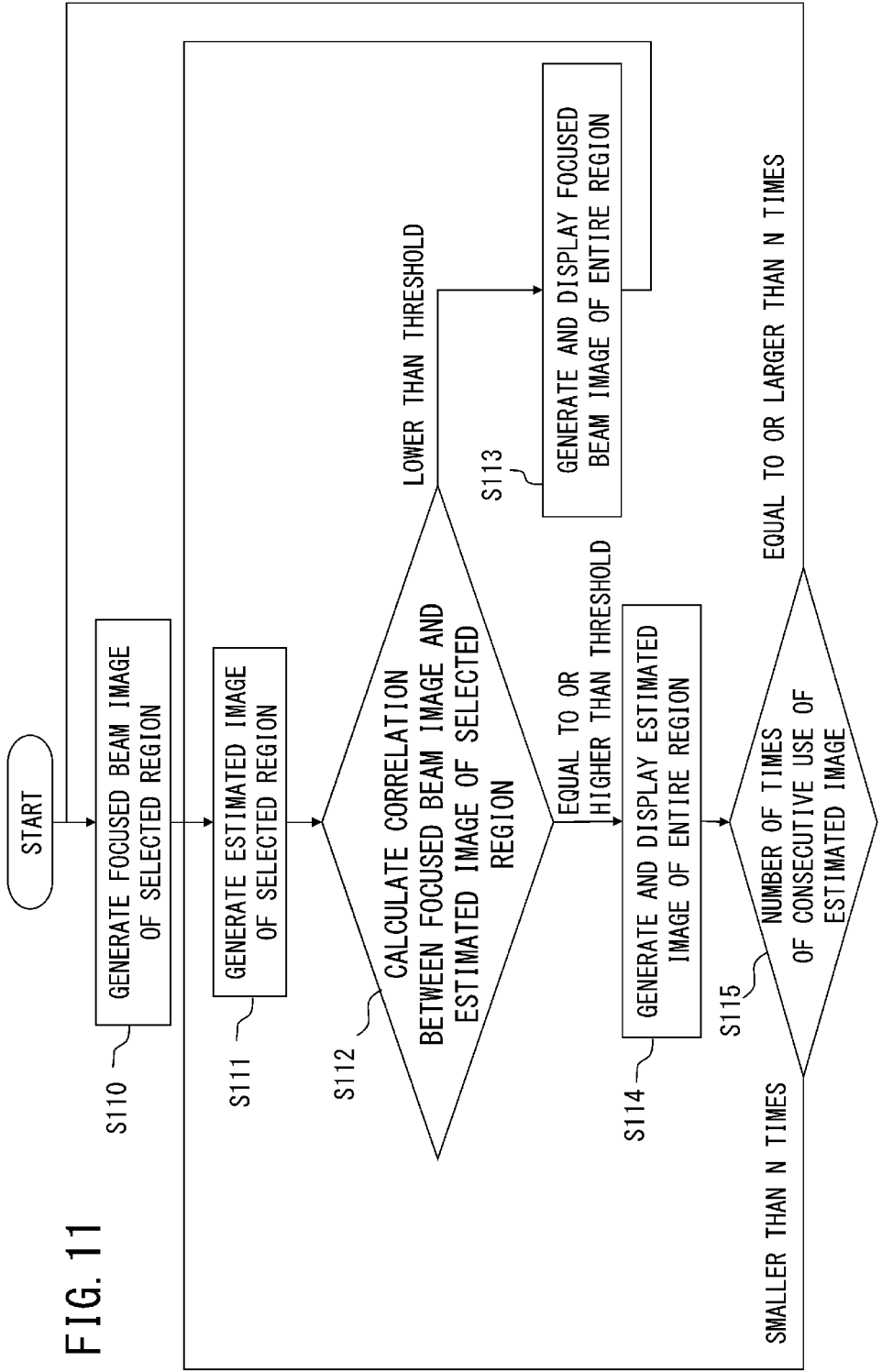
FIG. 11 is another diagram representing a flow of processing according to the second embodiment.

FIG. 11 shows an example of control for using an image in the selected region for estimating a correlation. In step S110, only the selected region is scanned by a focused beam and a focused beam image of the selected region is generated. This image is not used for display. In step S111, a plane-wave beam image is imaged and an estimated image of the selected region is calculated from the plane-wave beam image. In step S112, the system control block 109 calculates a correlation between the focused beam image of the selected region and the estimated image of the selected region. When the correlation is lower than a threshold, in step S113, a focused beam image of the entire observation region is generated and displayed. Subsequently, a return is made to step S111. On the other hand, when correlation between the focused beam image and the estimated image of the selected region is at least the threshold, in step S114, a plane-wave beam image of the entire observation region is imaged and an estimated image of the entire observation region is generated from the plane-wave beam image and displayed. Steps S111 to S114 are repeated until the number of times the estimated image was consecutively used reaches N times, and once the number of times reaches N times, a return is made to step S110 (step S115). By performing such control, since the time required to acquire images (a focused beam image and an estimated image) to be used to evaluate a correlation can be significantly reduced, efficiency of processing can be improved.

Next, control in a case where an instruction to save a still image or a moving image is issued by the user during an imaging operation will be described. When receiving an instruction to save a still image, the system control block 109 may save a focused beam image and/or an estimated image acquired at a time point that is closest to a timing at which the instruction had been received. At this point, images having been acquired but not used for display may be excluded from objects to be saved. For example, when an instruction to save a still image is input to the system control block 109 through a GUI or the like at a timing t1 shown in FIG. 9B, the focused beam image acquired at time B1 and the estimated image acquired at time P1 are saved. In this case, the two images may be presented to the user as candidates to be saved and the user may be asked to select an actual image to be saved. In addition, for example, when an instruction to save a still image is input at a timing t2, the focused beam image acquired at time B2 and the estimated image acquired at time P2 which is a time point that is closest to the timing t2 and which is also an estimated image having been used for display are saved. Since the estimated image obtained at time P3 has a correlation that is lower than the threshold and the estimated image has not been used for display, the estimated image is excluded from objects to be saved. With respect to images to be saved, a setting that causes only focused beam images to be saved or only estimated images to be saved can be separately configured as an option of the system. Furthermore, when a save instruction is issued, the flow charts shown in FIGS. 10 and 11 may be interrupted to perform control for imaging a focused beam image and the image may be saved.

In addition, with respect to saving a moving image, a focused beam image and an estimated image may be saved separately or saved in a mixed manner Switching between these save methods can also be set as an option of the system. Furthermore, since a frame rate of an image changes depending on control in the image generation method according to the present embodiment, when saving a moving image, interpolation and processing may be applied so as to create data at constant time intervals and a moving image with a constant frame rate may be subsequently saved.

While control for adaptively switching between a focused beam image and an estimated image based on a correlation of images has been described in the present embodiment, a ratio of the images may be fixed or the system control block 109 may perform control so that the ratio can be interactively changed by the user from a GUI. In addition, when there are consecutive estimated images and a correlation between estimated images that are separated from each other by a least one estimated image is high, a determination may be made that an object has hardly moved and a switch to a focused beam image may be automatically made. Accordingly, an image by transmission of a focused beam can be obtained with respect to the object that has hardly moved.

Other Embodiments

The embodiments described above merely represent specific examples of the present invention. A scope of the present invention is not limited to the configurations of the embodiments described above and various embodiments can be adopted without departing from the spirit of the invention.

For example, while a model using a plane-wave beam image as input data and an estimated image as output data has been used in the first and second embodiments, an input and an output of a model need not be images. For example received data obtained by transmission of a plane-wave beam may be used as-is as input data or received data after being subjected to phasing addition processing may be used as input data. In addition, as ground truth data, received data obtained by transmission of a focused beam may be used as-is or received data after being subjected to phasing addition processing may be used. A similar operational effect to the embodiments described above can be produced even when using such models.

Furthermore, the disclosed technique can take the form of an embodiment of, for example, a system, an apparatus, a method, a program, or a recording medium (a storage medium). Specifically, the disclosed technique may be applied to a system constituted by a plurality of devices (for example, a host computer, an interface device, an imaging apparatus, and a web application) or to an apparatus constituted by a single device.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present invention, an ultrasonic diagnostic apparatus that enables an image with good image quality to be obtained while realizing a high frame rate can be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-009941, filed on Jan. 24, 2020, which is hereby incorporated by reference herein in its entirety.

What is claimed is:

1. An ultrasonic diagnostic apparatus, comprising:
an ultrasonic probe configured to transmit and receive ultrasonic waves to and from an observation region of an object;
a memory storing a program; and
one or more processors which, by executing the program, function as:
an estimated image generating unit configured to generate estimated image data corresponding to first image data obtained by transmission of an ultrasonic focused beam from second image data obtained by transmission of an ultrasonic plane-wave beam by using a model having been machine-learned from learning data including the second image data obtained by the transmission of the ultrasonic plane-wave beam and the first image data obtained by the transmission of the ultrasonic focused beam,
wherein the first image data obtained by the transmission of the ultrasonic focused beam is ground truth data corresponding to the second image data obtained by the transmission of the ultrasonic plane-wave beam, and
wherein the model has been machine-learned regarding a correlation between the first image data obtained by the transmission of the ultrasonic focused beam and the second image data obtained by the transmission of the ultrasonic plane-wave beam based on a plurality of pieces of learning data.

2. The ultrasonic diagnostic apparatus according to claim 1, wherein the second image data obtained by the transmission of the ultrasonic plane-wave beam and/or the first image data obtained by the transmission of the ultrasonic focused beam includes radio frequency (RF) data.

3. The ultrasonic diagnostic apparatus according to claim 1, wherein the estimated image generating unit generates the estimated image data from third image data obtained using a signal obtained by combining a plurality of received signals respectively obtained by a plurality of transmissions of the ultrasonic plane-wave beam.

4. The ultrasonic diagnostic apparatus according to claim 1, wherein the one or more processors which, by executing the program, further function as:
an image generating unit configured to generate focused beam image data that is obtained by performing transmission of the ultrasonic focused beam by the ultrasonic probe.

5. The ultrasonic diagnostic apparatus according to claim 4, wherein the one or more processors which, by executing the program, further function as:
a control unit configured to perform control of a display image to be output to a display apparatus,
wherein the control unit has a display mode in which the display image is updated using the estimated image data.

6. The ultrasonic diagnostic apparatus according to claim 5, wherein the display mode includes a mode that enables the display image to be updated at a higher frame rate than a case where the display image is updated using the focused beam image data without using the estimated image data.

7. The ultrasonic diagnostic apparatus according to claim 5, wherein the control unit has a second display mode in which the estimated image data and the focused beam image data are displayed side by side.

8. The ultrasonic diagnostic apparatus according to claim 1, wherein the first image data which is included in the learning data and which is obtained by the transmission of the ultrasonic focused beam is data representing a received signal per se of the ultrasonic waves by the ultrasonic probe or data representing a phasing addition of the received signal.

9. The ultrasonic diagnostic apparatus according to claim 1, wherein the model is a neural network.

10. The ultrasonic diagnostic apparatus according to claim 1, wherein the learning data includes a transmission angle and/or a number of transmissions of the ultrasonic plane-wave beam in the transmission of the ultrasonic plane-wave beam.

11. A learning apparatus performing machine learning of the model to be used by the estimated image generating unit of the ultrasonic diagnostic apparatus according to claim 1, the learning apparatus performing the machine learning of the model by using the learning data that includes the second image data, obtained by the transmission of the ultrasonic plane-wave beam, as input data and the first image data, obtained by the transmission of the ultrasonic focused beam, as the ground truth data.

12. A learning apparatus, comprising:
a memory storing a program; and
one or more processors which, by executing the program, function as:
 a learning unit configured to perform machine learning of a model by using learning data that includes second image data, obtained by transmission of an ultrasonic plane-wave beam, as input data and first image data, obtained by transmission of an ultrasonic focused beam, as ground truth data,
 wherein the first image data obtained by the transmission of the ultrasonic focused beam is the ground truth data corresponding to the second image data obtained by the transmission of the ultrasonic plane-wave beam, and
 wherein the model has been machine-learned regarding a correlation between the first image data obtained by the transmission of the ultrasonic focused beam and the second image data obtained by the transmission of the ultrasonic plane-wave beam based on a plurality of pieces of learning data.

13. The learning apparatus according to claim 12, wherein the input data includes a transmission angle and/or a number of transmissions of the ultrasonic plane-wave beam in the transmission of the ultrasonic plane-wave beam.

14. An image processing method, comprising:
 transmitting and receiving ultrasonic waves to and from an observation region of an object by an ultrasonic probe; and
 generating estimated image data corresponding to first image data obtained by transmission of an ultrasonic focused beam from second image data obtained by transmission of an ultrasonic plane-wave beam by using a model having been machine-learned from learning data including the second image data obtained by the transmission of the ultrasonic plane-wave beam and the first image data obtained by the transmission of the ultrasonic focused beam,
 wherein the first image data obtained by the transmission of the ultrasonic focused beam is ground truth data corresponding to the second image data obtained by the transmission of the ultrasonic plane-wave beam, and
 wherein the model has been machine-learned regarding a correlation between the first image data obtained by the transmission of the ultrasonic focused beam and the second image data obtained by the transmission of the ultrasonic plane-wave beam based on a plurality of pieces of learning data.

15. A non-transitory computer readable medium storing a program causing a computer to execute an image processing method, the image processing method comprising:
 transmitting and receiving ultrasonic waves to and from an observation region of an object by an ultrasonic probe; and
 generating estimated image data corresponding to first image data obtained by transmission of an ultrasonic focused beam from second image data obtained by transmission of an ultrasonic plane-wave beam by using a model having been machine-learned from learning data including the second image data obtained by the transmission of the ultrasonic plane-wave beam and the first image data obtained by the transmission of the ultrasonic focused beam,
 wherein the first image data obtained by the transmission of the ultrasonic focused beam is ground truth data corresponding to the second image data obtained by the transmission of the ultrasonic plane-wave beam, and
 wherein the model has been machine-learned regarding a correlation between the first image data obtained by the transmission of the ultrasonic focused beam and the second image data obtained by the transmission of the ultrasonic plane-wave beam based on a plurality of pieces of learning data.

16. An ultrasonic diagnostic apparatus, comprising:
 an ultrasonic probe configured to transmit and receive ultrasonic waves to and from an observation region of an object;
 a memory storing a program; and
 one or more processors which, by executing the program, function as:
  an estimated image generating unit configured to generate estimated image data corresponding to first image data obtained by transmission of an ultrasonic focused beam from second image data obtained by transmission of an ultrasonic plane-wave beam by using a model having been machine-learned from learning data including the second image data obtained by the transmission of the ultrasonic plane-wave beam and the first image data obtained by the transmission of the ultrasonic focused beam, and
  a control unit configured to perform control of a display image to be output to a display apparatus, wherein the control unit updates the display image by the first image data obtained by the transmission of the ultrasonic focused beam, at least one of in a case where the second image data obtained by the transmission of the ultrasonic plane-wave beam does not satisfy a prescribed condition and in a case where a number of consecutive updates of the display image using the estimated image data reaches a prescribed number of times.

* * * * *